(12) United States Patent
Anderson et al.

(10) Patent No.: US 7,132,080 B2
(45) Date of Patent: Nov. 7, 2006

(54) MODULE FOR AUTOMATED MATRIX REMOVAL

(75) Inventors: Marc R. Anderson, Sunnyvale, CA (US); Michael J. West, Sunnyvale, CA (US); James Tappan, Sunnyvale, CA (US)

(73) Assignee: Metara, Inc., Sunnyvale, CA (US)

( * ) Notice: Subject to any disclaimer, the term of this patent is extended or adjusted under 35 U.S.C. 154(b) by 0 days.

(21) Appl. No.: 10/641,946

(22) Filed: Aug. 15, 2003

(65) Prior Publication Data

US 2005/0036917 A1  Feb. 17, 2005

(51) Int. Cl.
*B01L 3/00* (2006.01)

(52) U.S. Cl. ............... 422/99; 422/267; 422/100; 422/101; 210/416.1; 210/791; 210/767; 210/198.1; 436/177; 436/188

(58) Field of Classification Search ............... 436/63, 436/177, 178; 422/99–102, 267; 210/198.1, 210/416.1, 791, 767
See application file for complete search history.

(56) References Cited

U.S. PATENT DOCUMENTS 6,007,777 A * 12/1999 Purcell et al. ............... 422/80
6,291,249 B1 * 9/2001 Mahant et al. ............. 436/177
6,692,968 B1 * 2/2004 Burshteyn et al. ........... 436/63

* cited by examiner

*Primary Examiner*—Jill Warden
*Assistant Examiner*—Jyoti Nagpaul
(74) *Attorney, Agent, or Firm*—Jonathan W. Hallman; MacPherson Kwok Chen & Heid LLP

(57) ABSTRACT

An automated matrix removal module is configurable to automatically withdraw a portion of sample containing an interferent. The module is further configurable to mix the portion of sample with a precipitating reagent selected to react with the interferent to form a precipitant and then filter mixture of sample and precipitant reagent through a filter. Finally, the module is further configurable to flush the precipitant from the filter.

21 Claims, 2 Drawing Sheets

MODULE FOR AUTOMATED MATRIX REMOVAL

TECHNICAL FIELD

The present invention relates generally to chemical analysis, and more particularly to apparatus for the removal of chemical interferents prior to chemical analysis.

BACKGROUND

Automated systems for measuring the concentration of analytes in a sample have been developed using a number of analytical techniques such as chromatography or mass spectrometry. For example, co-assigned U.S. patent application Ser. No. 10/094,394, entitled "A Method and Apparatus for Automated Analysis and Characterization of Chemical Constituents of Process Solutions," filed Mar. 8, 2002, the contents of which are hereby incorporated by reference in their entirety, discloses an automated in-process mass spectrometry (IPMS) apparatus for identifying and quantifying chemical constituents and their reaction products in process solutions.

One type of process solution which the IPMS apparatus in the above-mentioned application may analyze is a copper electroplating bath for the deposition of copper structures on semiconductor wafers. The bath comprises a relatively concentrated acidic aqueous copper sulfate solution. Plating topology is controlled by organic plating solution additives within the copper sulfate solution that function to either suppress or accelerate the plating process. These additives experience electrochemical breakdown during the plating process and can be lost by drag out or by becoming trapped within the film. However, the achievement of void-free plating in the vias and trenches of sub-micron high-aspect-ratio structures requires very tight control of additive levels. Unlike indirect measurement methods such as cyclic voltametric stripping (CVS) that monitor the effectiveness of the plating solution, the IPMS apparatus discussed above allows a user to directly measure the additive concentration plus the breakdown products in the electroplating bath to ensure a defect-free deposition process.

High sensitivity quantification of the organic additives and their breakdown by-products in the electroplating bath is hampered by the relatively high concentration of sulfuric acid and copper sulfate matrix within the bath. These relatively high concentrations of sulfuric acid, plus sulfate and copper ions obscure the detection and quantification of the organic additive ions because ionization of the higher concentration ions is statistically more likely in the ionization source of the mass spectrometer. Thus, the copper sulfate should be removed from the sample and/or the pH adjusted to quantify the organic additive concentration. Similarly, other metrology techniques such as flow injection analysis and chromatography often require the removal of chemical constituents that may hamper the quantification of an analyte of interest.

Accordingly, there is a need in the art for automated systems for the removal of chemical interferents prior to a chemical analysis.

SUMMARY

In accordance with the present invention, an analytical apparatus for the automated removal of an interferent from a solution containing an analyte of interest includes a pump; a source of precipitating reagent, the precipitating reagent being reactive with the interferent to form a precipitate; a reaction vessel; and a filter to protect sensitive analytical hardware. The analytical apparatus may be configured into a first configuration wherein the pump may pump a volume of the solution containing the analyte of interest and a volume of the precipitating reagent into the reaction vessel. In this fashion, the precipitating reagent and the interferent may react within the reaction vessel to form a precipitant. To filter the contents of the reaction vessel, the analytical apparatus may be configured into a second configuration allowing the pump to pump the contents of the reaction vessel through the filter. The analytical apparatus may further be configured into a third configuration allowing the filter and the reaction vessel to be flushed with a solvent. The flushing solvent may be a reagent selected to dissolve the precipitate. Advantageously, the analytical apparatus may repeatedly cycle through the first through third configurations, thereby operating to continuously receive a sample, react the sample with the precipitating reagent, filter the resulting precipitant from the sample, and flush the filter.

BRIEF DESCRIPTION OF THE DRAWINGS

Use of the same reference symbols in different figures indicates similar or identical items.

DETAILED DESCRIPTION

Figure 1:
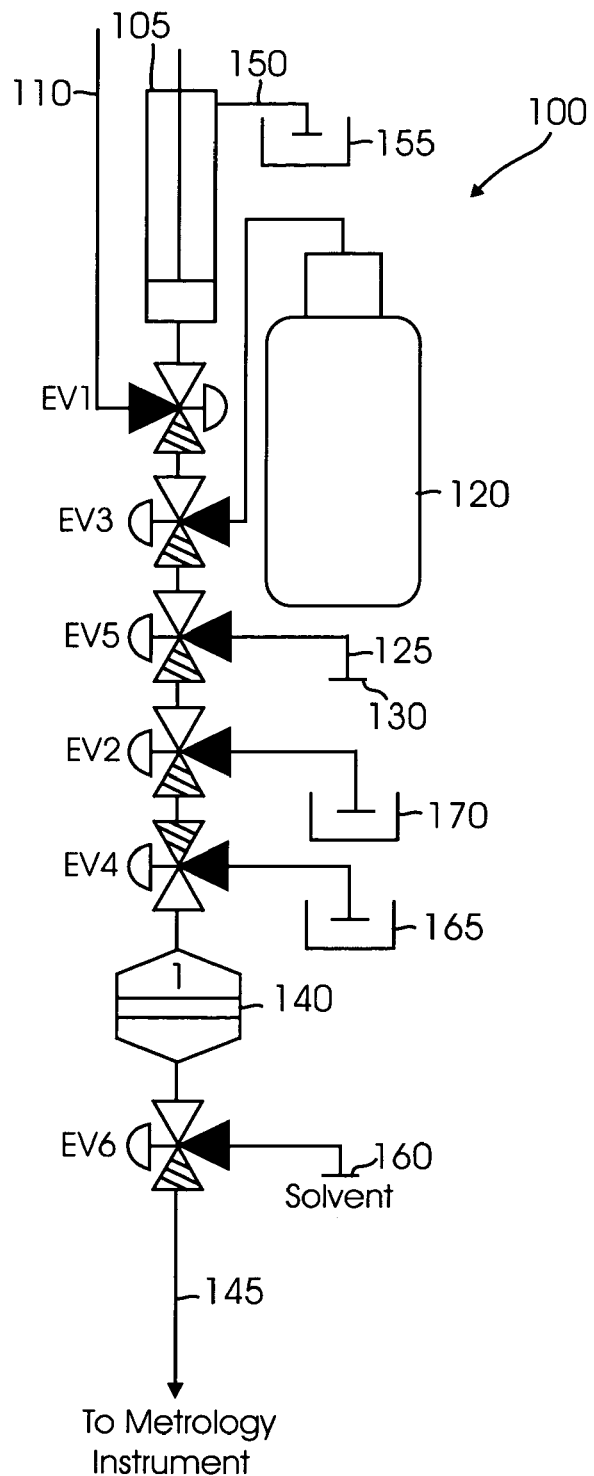
FIG. 1 is a schematic illustration of a matrix removal module according to one embodiment of the invention.

FIG. 1 illustrates an automated matrix removal module 100. Module 100 includes a pump such as syringe pump 105. Syringe pump 105 is connected to a conduit 110 when a three-way valve EV1 is properly actuated. Conduit 110 is connected to a source (not illustrated) of a sample solution containing an analyte which will be quantified by a chemical metrology instrument (also not illustrated) after processing by module 100. Typical chemical metrology instruments include mass spectrometers, chromatography systems such as high performance liquid chromatography (HPLC), and flow injection analysis (FIA) systems. It will be appreciated, however, that the present invention is not limited by the type of chemical metrology instrument used after processing by module 100.

Regardless of the type of chemical metrology instrument that will be used to characterize the analyte of interest in the sample solution, the performance of this instrument will be hampered by the presence of a chemical interferent in the sample solution. As used herein, "chemical interferent" will be understood to denote a constituent within the sample solution that hampers analysis of the analyte of interest by the chemical metrology tool. For example, as discussed earlier, copper sulfate and sulfuric acid act as chemical interferents in the characterization of organic additives within a copper electroplating solution by a mass spectrometer. This interference results from the copper and sulfate ions being preferentially ionized within the mass spectrometer, thereby obscuring the measurement of the organic additive concentration. The acid and copper sulfate interferents may also be denoted as a "matrix" which must be eliminated or removed before characterization of the organic additives. In general, an interferent may comprise a plurality of chemical species.

To begin the process of removing the chemical interferent from the sample solution, three-way valve EV1 is actuated so that as the plunger of syringe pump 105 is withdrawn, a portion of the sample carried by conduit 110 is drawn into syringe pump 105. Syringe pump 105 may be controlled by a stepper motor (not illustrated) to precisely control the amount of sample withdrawn into syringe pump 105. A precipitating reagent solution may then be added to the contents of syringe pump 105 as follows. The appropriate precipitating reagent solution is provided by a precipitating reagent source 120 connected to three-way valve EV3. The precipitating reagent is selected such that it will react with the chemical interferent to produce a solid precipitant. For example, if the chemical interferent is aqueous copper sulfate and sulfuric acid, one suitable precipitating reagent solution would be aqueous barium hydroxide. As another example, if the interferent comprises $Ag^+$ ions in an aqueous sample, a precipitating reagent would comprise a source of $CL^-$ ions such as NaCl. With respect to the removal of copper sulfate from an aqueous solution using barium hydroxide, a solution of barium hydroxide at an appropriate concentration mixed with the syringe pump contents would produce $Cu(OH)_2$ and $BaSO_4$. Both of these compounds are relatively insoluble in aqueous solution and would thus precipitate out of the solution within the syringe pump. To mix the contents of syringe pump 105 with the precipitating reagent solution, three-way valves EV1 and EV3 are actuated to connect syringe pump 105 to precipitating reagent source 120. The plunger of syringe pump 105 may then be withdrawn an additional amount to add the appropriate amount of precipitating reagent solution to the contents of syringe pump 105. To aid the flow of precipitating reagent solution into syringe pump 105, precipitating reagent solution source 120 may be pressurized with an inert gas such as nitrogen. Alternatively, a mechanical pump may be used to assist the flow of precipitating reagent solution into three-way valve EV3.

After the addition of precipitating reagent solution into syringe pump 105, additional solvent may be optionally added to flush the three-way valves of precipitating reagent. For example, in the case of removing a copper sulfate matrix as discussed above, the additional solvent would be ultra pure water (UPW). In the exemplary embodiment for module 100 shown in FIG. 1, this additional solvent is supplied by a source 130 connected to conduit 125 that in turn connects to three-way valve EV5. By appropriate actuation of three-way valves EV1, EV3, and EV5, source 130 is connected to syringe pump 105 such that as the plunger of syringe pump 105 is withdrawn, a predetermined amount of solvent may be added to the contents of syringe pump 105. Source 130 may also be pressurized with an inert gas such as nitrogen to aid in the injection of solvent into three-way valve EV5. After any addition of solvent to syringe pump 105, the contents of syringe pump 105 may be further processed by, for example, heating, cooling, or by simply waiting to aid in the formation of precipitate as required. With respect to precipitation of $Cu(OH)_2$ and $BaSO_4$ as discussed above, no heating or cooling of the syringe pump 105 is necessary.

After formation of the precipitation within syringe pump 105, syringe pump 105 may pump its contents through a filter 140. Before syringe pump 105 may pump its contents through filter 140, three-way valves EV1, EV3, EV5, EV2, and EV4 are actuated to connect syringe pump 105 to filter 140. After this connection, the plunger of syringe pump 105 is depressed a certain amount to filter a portion or all of the syringe contents through filter 140. The pore size for filter 140 is chosen appropriately as determined by the flow rate, solvent, and expected type of precipitate that will be filtered by filter 140. For example, to filter the $Cu(OH)_2$ and $BaSO_4$ precipitants discussed previously, a suitable pore size for filter 140 is approximately 0.45 um. By proper actuation of three-way valve EV6, the filtered contents pass through filter 140 into conduit 145 for eventual processing by a chemical metrology instrument (not illustrated).

Although filter 140 will have thus removed any solid precipitate in the filtered solution provided to the chemical metrology instrument, unfiltered solution and precipitate will now be contaminating module 100. Thus, module 100 should be flushed as follows before another cycle of receiving a sample, mixing the sample with a precipitating reagent, and filtering the mixed solution may begin. To begin the flush cycle, the plunger of syringe pump 105 is withdrawn a sufficient amount to expose a backflush port 150 in the body of syringe pump 105. Prior to the flush cycle, the plunger of syringe pump 105 is not withdrawn to such a degree so as to expose backflush port 150. However, during the flush cycle, backflush port 150 is exposed by a sufficient withdrawal of the plunger. With backflush port 150 exposed, three-way valves EV5, EV3, and EV1 are actuated so that solvent source 130 is connected to syringe pump 105. Because solvent source 130 is pressurized, solvent will then flush from solvent source 130 through backflush port 150 into drain 155. Alternatively, a mechanical pump may be used to force solvent into three-way valve EV5 and eventually to drain 155.

While syringe pump 105 is flushed, filter 140 may also be flushed. To flush filter 140, three-way valves EV6 and EV4 are actuated to connect solvent source 160 to drain 165. Because solvent source 160 is pressurized with an inert gas such as nitrogen, solvent will then flow into three-way valve EV6, through filter 140 and three-way valve EV4 into drain 165, thereby flushing filter 140 of the precipitate from the previous filtering cycle. To complete the flushing cycle, three-way valves EV1, EV3, EV5, and EV2 are actuated to connect syringe pump 105 to drain 170. The plunger of syringe pump 105 is then depressed. Because syringe pump 105 will have been filled with clean solvent after sufficient flushing through backflush port 150, clean solvent will then flush through three-way valve EV2 into drain 170, thereby flushing three-way valve EV2. It will be appreciated that the presence of drain 170 is a result of the use of three-way valves—three-way valve EV4 cannot be actuated so as to connect drain 165 to syringe pump 105. Thus, after flushing syringe pump 105, its contents must be emptied into another drain such as drain 170. In alternative embodiments that do not use three-way valves, this extra drain would be unnecessary. For example, one or more two-position multi-way valves such as rotary valves could be employed to alternatively connect syringe pump 105 to the sample source, to the precipitating reagent source 120, to filter 140, and finally to a drain.

Consider the advantages provided by module 100. Because the various components may all be actuated according to commands from a microprocessor or state machine, the operation is entirely automated and requires no human intervention. Moreover, because of the flush cycle, filter 140 may be reused for many cycles, thereby keeping operation costs low.

Figure 2:
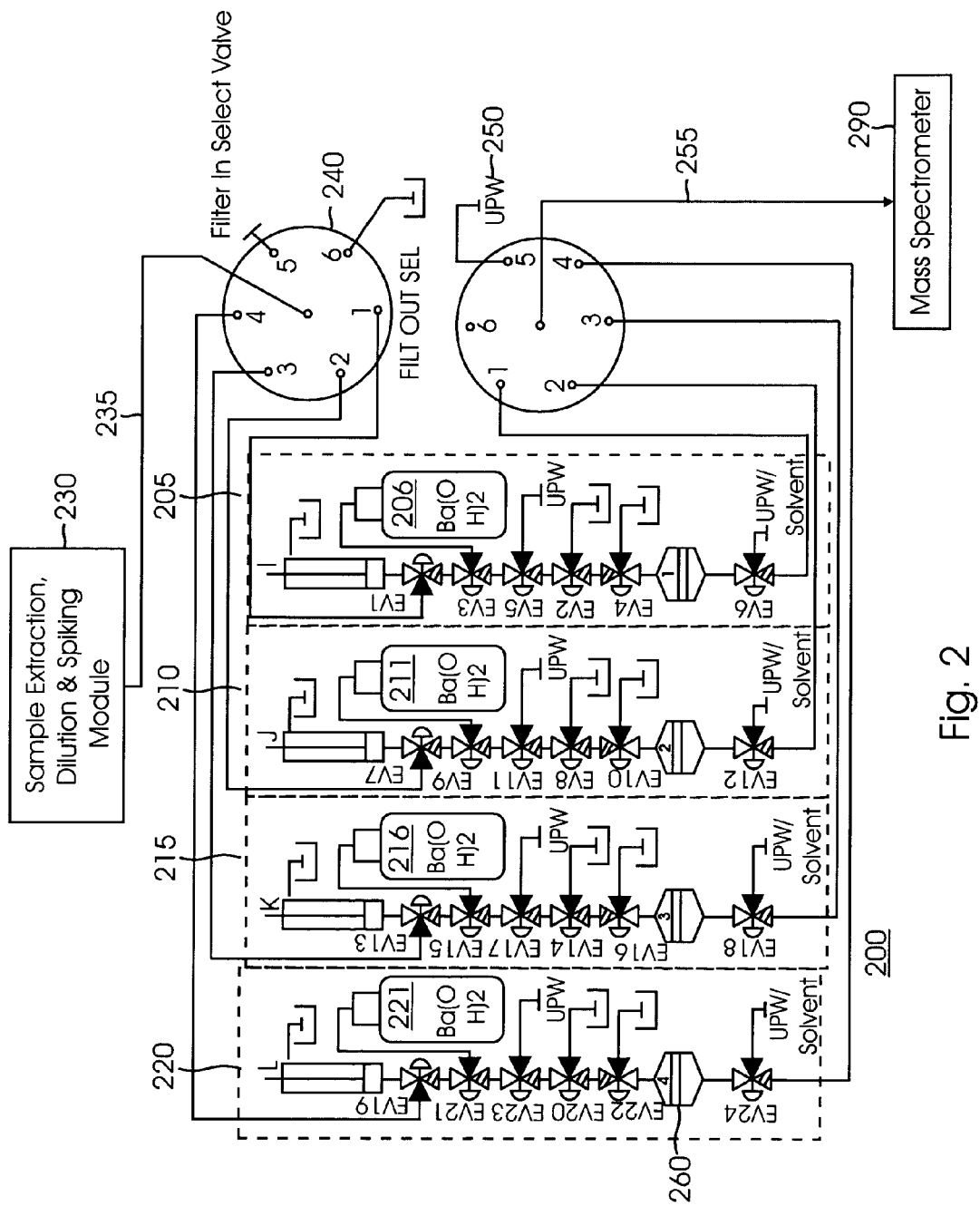
FIG. 2 is a schematic illustration of an IPMS system incorporating multiple matrix removal modules according to one embodiment of the invention.

Multiple automated matrix elimination modules such as module 100 may be employed in a chemical metrology system. For example, exemplary system 200 includes modules 205, 210, 215, and 220 as shown in FIG. 2. Each of modules 205 through 220 functions analogously as described for module 100 of FIG. 1. In system 200, the chemical metrology instrument is a mass spectrometer 290. A sample extraction, dilution, and spiking module 230 extracts a sample. For example, the module 230 may comprise a sample extraction module as described in co-assigned U.S. application Ser. No. 10/086,025, filed Feb. 28, 2002, the contents of which are hereby incorporated by reference. In addition, module 230 may comprises a dilution and spiking module having a dual-loop multi-way valve for the simultaneous mixing of a portion of the sample with an appropriate spike and diluent as described in co-assigned U.S. application Ser. No. 10/641,480, entitled "Loop Dilution System," concurrently filed herewith, the contents of which are hereby incorporated by reference. After processing through module 230, a spiked and diluted sample is provided on conduit 235 to a "filter in" selection valve 240 that determines which matrix elimination module will receive the spiked and diluted sample. System 200 is specialized for the analysis of organic additives in a copper electroplating bath. Thus, each module 220 through module 205 uses an aqueous solution of barium hydroxide as the precipitating reagent solution. However, depending upon the organic additive being characterized, the concentration of barium hydroxide in the precipitating reagent solution should be varied. For example, the additive (bis(3-sulfopropyl) disulfide (SPS) is preferentially characterized in a slightly acidic environment whereas the additive polyethylene glycol (PEG) is preferentially characterized in a slightly basic environment. To remove a copper sulfate/sulfuric acid matrix from a diluted and spiked sample for an SPS analysis, the barium hydroxide concentration should be such that the sulfuric acid is not entirely neutralized so as to leave the treated solution slightly acidic. Conversely, to remove a copper sulfate/sulfuric acid matrix from a diluted and spiked sample for a PEG analysis, the barium hydroxide concentration should be such that the sulfuric acid is completely neutralized with a slight excess of barium hydroxide so as to leave the treated solution slightly basic. Accordingly, modules 220, 215, 210, and 205 are configured with differing concentrations of barium hydroxide solution in reservoirs 221, 216, 211, and 206, respectively, to provide the desired concentrations of barium hydroxide for the organic additive being characterized. Alternatively, the amount of barium hydroxide that may be added to the precipitation module may be controlled by the length of the withdrawing stroke on the plunger thereby effecting the final concentration of barium hydroxide in the precipitating syringe.

Depending upon which additive is being characterized, filter-in selection valve 240 selectively couples conduit 235 to modules 220 through 205 as desired. For example, suppose module 230 provides a diluted and spiked sample for an SPS module and that reservoir 221 in module 220 contains a relatively weak concentration of barium hydroxide. Selection valve 240 would thus be configured to connect conduit 235 to three-way valve EV19 in module 220. The plunger for syringe pump L may then be withdrawn to draw a portion of the diluted and spiked sample from conduit 235 into syringe pump L. After mixing with the relatively weak barium hydroxide solution from reservoir 221, the contents of syringe pump L should be slightly acidic to allow an accurate characterization of the SPS concentration in the original sample. Conversely, suppose module 230 provides a diluted and spiked sample for a PEG analysis to conduit 235 and reservoir 206 in module 205 contains a relatively concentrated barium hydroxide solution. Selection valve 240 would then be configured to connect three-way valve EV1 in module 205 to conduit 235. The plunger for syringe pump I may then be withdrawn to draw a portion of the diluted and spiked sample from conduit 235 into syringe pump I. After mixing with the relatively concentrated barium hydroxide solution from reservoir 206, the contents of syringe pump I should be slightly basic to allow an accurate characterization of the PEG concentration in the original sample. Depending upon which module 220 through 205 has been selected to perform the matrix removal, a filter out selection valve 250 selects for the output from the appropriate module. For example, if module 220 has performed the matrix removal, selection valve 250 is configured to connect conduit 255 to three way valve EV24. The plunger for syringe pump L would then be depressed to filter a portion of its contents through filter 260 and three-way valve EV24 into conduit 255. From conduit 255, the filtered solution is then analyzed by mass spectrometer 290.

The above-described embodiments of the present invention are merely meant to be illustrative and not limiting. For example, dilution module 100 of FIG. 1 may be modified by replacing syringe pump 105 with another type of pump. In addition, the three-way valves may be replaced by other valve means. It will thus be obvious to those skilled in the art that various changes and modifications may be made without departing from this invention in its broader aspects. Accordingly, the appended claims encompass all such changes and modifications as fall within the true spirit and scope of this invention.

What is claimed is:

1. An analytical apparatus for the automated removal of an interferent from a solution containing an analyte of interest, comprising:
   an at least one pump;
   a source of precipitating reagent, the precipitating reagent being reactive with the interferent to form a precipitate;
   a reaction vessel; and
   a filter, wherein the analytical apparatus has a first configuration allowing the at least one pump to pump a volume of the solution and a volume of the precipitating reagent into the reaction vessel, the analytical apparatus having a second configuration allowing the at least one pump to pump the contents of the reaction vessel through the filter in a first direction, the analytical apparatus having a third configuration allowing the filter and the reaction vessel to be flushed with a solvent, wherein the filter is flushed in an opposite direction to the first direction.

2. The analytical apparatus of claim 1, wherein the at least one pump is a single syringe pump, the reaction vessel being the body of the syringe pump.

3. The analytical apparatus of claim 2, wherein the syringe pump includes a backflush port, and wherein the analytical apparatus is configured in the third configuration such that the contents of the syringe pump are flushed into the backflush port.

4. The analytical apparatus of claim 3, further comprising a drain, wherein the analytical apparatus is configured in the third configuration such that the solvent flushes through the filter into the drain.

5. The analytical apparatus of claim 4, wherein the drain connects to the remaining components of the analytical apparatus through a three-way valve.

6. The analytical apparatus of claim 5, wherein the precipitating reagent source connects to the remaining components of the analytical apparatus though a three-way valve.

7. The analytical apparatus of claim 2, wherein the analytical apparatus is configured in the first configuration such that the syringe pump may pump solvent into the body of syringe pump to mix with the portion of the solution and the precipitating reagent.

8. The analytical apparatus of claim 1, wherein the analytical apparatus is responsive to electronic commands for controlling whether the analytical apparatus is in the first, second, or third configuration.

9. The analytical apparatus of claim 1, wherein the precipitating reagent source is a source of aqueous barium hydroxide.

10. The analytical apparatus of claim 9, wherein the interferent comprises copper sulfate.

11. The analytical apparatus of claim 9, wherein the interferent comprises sulfuric acid.

12. The analytical apparatus of claim 1, further comprising a chemical metrology instrument for analyzing the filtered solution.

13. The analytical apparatus of claim 12, wherein the chemical metrology instrument is a mass spectrometer.

14. An analytical apparatus, comprising:
a syringe pump;
a sample source, the sample containing an interferent;
a source of precipitating reagent, the precipitating reagent being reactive with the interferent to form a precipitant;
a filter;
means for configuring the syringe pump to mix a portion of the precipitating reagent from the source of precipitating reagent with a portion of the sample from the sample source;
means for configuring the syringe pump to pump a portion of its contents through the filter in a first direction; and
means for flushing the filter with solvent in a second direction opposite to the first direction.

15. The analytical apparatus of claim 14, further comprising:
means for flushing the syringe pump with the solvent.

16. The analytical apparatus of claim 15, wherein the solvent is ultra pure water.

17. The analytical apparatus of claim 15, wherein the means for flushing the syringe pump includes a backflush port in the syringe pump.

18. The analytical apparatus of claim 14, further comprising a chemical metrology instrument for analyzing the filtered solution.

19. The analytical apparatus of claim 18, wherein the chemical metrology instrument is a mass spectrometer.

20. The analytical apparatus of claim 18, wherein the chemical metrology instrument is a flow injection analysis instrument.

21. The analytical apparatus of claim 18, wherein the chemical metrology instrument is a chromatography instrument.

* * * * *